(12) United States Patent
Dollinger et al.

(10) Patent No.: US 6,747,044 B2
(45) Date of Patent: Jun. 8, 2004

(54) NEUROKININ ANTAGONISTS

(75) Inventors: Horst Dollinger, Ingelheim (DE); Franz Esser, Ingelheim (DE); Birgit Jung, Schwabenheim (DE); Kurt Schromm, Ingelheim (DE); Georg Speck, Ingelheim (DE)

(73) Assignee: Boehringer Ingelheim Pharma KG, Ingelheim (DE)

( * ) Notice: Subject to any disclaimer, the term of this patent is extended or adjusted under 35 U.S.C. 154(b) by 0 days.

(21) Appl. No.: 09/981,025

(22) Filed: Oct. 16, 2001

(65) Prior Publication Data

US 2002/0147219 A1 Oct. 10, 2002

Related U.S. Application Data

(60) Provisional application No. 60/250,541, filed on Dec. 1, 2000.

(30) Foreign Application Priority Data

Oct. 17, 2000 (DE) .......................................... 100 51 320

(51) Int. Cl.[7] ..................... A61K 31/445; C07D 211/98
(52) U.S. Cl. ........................................ 514/315; 546/244
(58) Field of Search ............................ 514/315; 546/244

(56) References Cited

FOREIGN PATENT DOCUMENTS

| WO | WO 96 32386 | | 10/1996 | |
| --- | --- | --- | --- | --- |
| WO | WO 97 32865 | | 9/1997 | |
| WO | WO 97/32865 | * | 9/1997 | ......... C07D/295/14 |

* cited by examiner

Primary Examiner—Shengjun Wang
(74) Attorney, Agent, or Firm—Robert P. Raymond; Michael Morris; Philip I. Datlow

(57) ABSTRACT

The invention relates to new compounds of formula I

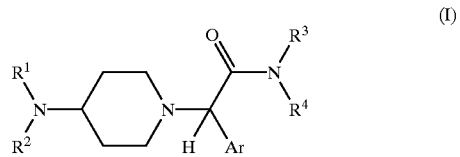

or the pharmaceutically acceptable salts thereof, wherein $R^1$ denotes 3-hydroxypropyl, 1,3-dihydroxyprop-2-yl or $C_3$–$C_6$-cycloalkylmethyl, and $R^2$, $R^3$, $R^4$ and Ar have the meanings given in the specification, as well as the preparation and use thereof. The new compounds are valuable neurokinin (tachykinin) antagonists.

27 Claims, No Drawings

NEUROKININ ANTAGONISTS

RELATED APPLICATION

Benefit of U.S. Provisional Application Serial No. 60/250,541, filed on Dec. 1, 2000 is hereby claimed, and said Provisional Application is herein incorporated by reference.

FIELD OF THE INVENTION

The invention relates to new compounds of formula I,

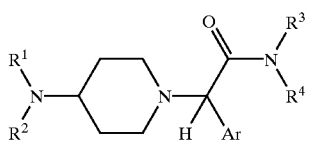

(I)

wherein the groups Ar, $R^1$, $R^2$, $R^3$ and $R^4$ have the meanings given in the claims and specification, processes for preparing them as well as their use as pharmaceutical compositions, and the pharmaceutically acceptable salts thereof, processes for preparing them and pharmaceutical compositions containing these compounds. The compounds are valuable neurokinin (tachykinin) antagonists.

BACKGROUND TO THE INVENTION

The compounds of formula I are partly covered by the broad general formula of International Patent Application WO97/32865. However, this does not disclose any compounds in which the piperidyl group in the 4 position is substituted by a 3-hydroxypropylamino, cycloalkylmethylamino or 1,3-dihydroxyprop-2-ylamino group. The compounds described in this international patent application are highly effective neurokinin antagonists with a broad spectrum of activity.

The problem of the present invention is to provide new neurokinin antagonists with an extended duration of activity. This problem is now solved according to the invention by the preparation of the new compounds of formula I.

DETAILED DESCRIPTION OF THE INVENTION

Surprisingly it has been found that the duration of activity of $NK_1$ receptor antagonists can be dramatically extended if an amino group of formula A

(A)

wherein $R^1$ denotes 3-hydroxypropyl, 1,3-dihydroxyprop-2-yl or $C_3-C_6$-cycloalkylmethyl, and $R^2$ denotes hydrogen, $C_1-C_6$-Alkyl, ω-hydroxy-$C_2-C_4$-alkyl, 1,3-dihydroxyprop-2-yl or $C_3-C_6$-cycloalkylmethyl, is inserted into these compounds.

The invention therefore relates to the use of an $NK_1$ receptor antagonist which contains an amino group of formula A,

(A)

wherein $R^1$ denotes 3-hydroxypropyl, 1,3-dihydroxyprop-2-yl or $C_3-C_6$-cycloalkylmethyl, and $R^2$ denotes hydrogen, $C_1-C_6$-alkyl, ω-hydroxy-$C_2-C_4$-alkyl, 1,3-dihydroxyprop-2-yl or $C_3-C_6$-cycloalkylmethyl, or the pharmaceutically acceptable salts thereof, for preparing a medicament with an extended period of activity for the treatment and prevention of neurokinin-mediated illnesses.

The invention further relates to new compounds of formula I

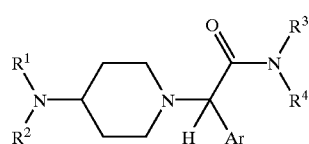

(I)

or the pharmaceutically acceptable salts thereof, wherein $R^1$ denotes 3-hydroxypropyl, 1,3-dihydroxyprop-2-yl or $C_3-C_6$-cycloalkylmethyl, $R^2$ denotes hydrogen, $C_1-C_6$-alkyl, ω-hydroxy-$C_2-C_4$-alkyl, 1,3-dihydroxyprop-2-yl or $C_3-C_6$-cycloalkylmethyl, Ar denotes unsubstituted phenyl or phenyl which is 1- to 5-substituted by halogen, hydroxy, $C_1-C_4$-alkyl, $C_1-C_4$-alkoxy, $C_1-C_4$-fluoroalkyl, $C_1-C_4$-fluoroalkoxy or —$OCH_2O$—;

$R^3$ denotes phenyl-$C_1-C_4$-alkyl, wherein the phenyl group may be substituted by 1 to 3 substituents, wherein the substituents independently of one another are selected from among halogen, hydroxy, $C_1-C_4$-alkyl, $C_1-C_4$-alkoxy, $C_1-C_4$-fluoroalkyl, $C_1-C_4$-fluoroalkoxy; and $R^4$ denotes hydrogen, $C_1-C_4$-alkyl, $C_3-C_8$-cycloalkyl, $CH_2COOH$, —$CH_2C(O)NH_2$, —OH or phenyl-$C_1-C_4$-alkyl.

In the foregoing and in what is to follow, the terms "alkyl" and "alkoxy" as used with reference to the groups $R^1$, $R^2$, $R^3$, $R^4$ or the substituents of Ar denote straight-chain or branched, saturated hydrocarbon groups with up to 6 carbon atoms, preferably 1 to 4 carbon atoms, particularly methyl, ethyl, n-propyl, i-propyl, n-butyl, tert-butyl, methoxy, ethoxy, n-propoxy or i-propoxy.

In the foregoing and in what is to follow, the term "cycloalkyl" as used with reference to the groups $R^1$, $R^2$ and $R^4$ denotes a cycloalkyl group with up to 8 carbon atoms, preferably 3 to 6 carbon atoms, particularly cyclopropyl, cyclopentyl or cyclohexyl.

In the foregoing and in what is to follow, the terms "fluoroalkyl" and "fluoroalkoxy" as used with reference to the group $R^3$ or the substituents of Ar denote straight-chain or branched, fluorine-substituted hydrocarbon groups with up to 4 carbon atoms and up to 9 fluorine atoms, preferably 1 or 2 carbon atoms and up to 5 fluorine atoms, particularly trifluoroethyl, pentafluoroethyl, 2,2,2-trifluoroethyl, 2-fluoroethyl, difluoromethoxy, trifluoromethoxy, pentafluoroethoxy, 2,2,2-trifluoroethoxy or 2-fluoroethoxy.

The compounds according to the invention are valuable neurokinin (tachykinin) antagonists which have substance P-antagonistic properties. They are useful for treating and preventing neurokinin-mediated illnesses and additionally have a long-lasting effect.

Compounds of general formula I may have acid groups, mainly carboxyl groups, and/or basic groups such as, for example, amino functions. Compounds of general formula I may therefore be in the form of internal salts, salts with pharmaceutically useable inorganic acids such as hydrochloric acid, sulphuric acid, phosphoric acid, sulphonic acid or organic acids (such as for example maleic acid, fumaric acid, citric acid, tartaric acid or acetic acid) or salts with pharmaceutically useable bases such as alkali or alkaline earth metal hydroxides or carbonates, zinc or ammonium hydroxides or organic amines such as, for example, diethylamine, triethylamine, triethanolamine etc.

The compounds according to the invention may occur as racemates, or they may be obtained as pure enantiomers, i.e. in the (R)- or (S)-form. Compounds which occur as racemates or as the (S)-form are preferred.

The compounds according to the invention are valuable neurokinin (tachykinin)-antagonists which have substance P-antagonistic properties. They are useful for treating and preventing neurokinin-mediated illnesses:

Treatment or prevention of inflammatory and allergic complaints of the airways, such as asthma, chronic bronchitis, hyperreactive airways, emphysema, rhinitis, COPD, pulmonary hypertension, cystic fibrosis, coughs;

of the eyes, such as conjunctivitis and iritis;

of the skin, such as dermatitis in contact eczema, neurodermatitis, pruritus, urticaria, psoriasis, sunburn, burns, insect bites, rosacea, itching, sensitive or hypersensitive skin, of the gastro-intestinal tract, such as gastric and duodenal ulcers, ulcerative colitis, Crohn's disease, inflammatory bowel disease, irritable colon, Hirschsprung's disease, motility problems;

of the joints or bones, such as rheumatoid arthritis, reactive arthritis, arthrosis, osteoporosis and Reiter's syndrome;

of the bladder, such as irritable bladder, incontinence, urinary urgency, urethritis, colic and cystitis, as well as restless leg syndrome.

Also for the treatment of diseases of the central nervous system such as dementia, Alzheimer's disease, schizophrenia, psychoses, anxiety states, alcohol or drug dependency, sexual dysfunctions, eating disorders, depression, headaches (e.g. migraine or tension headaches), epilepsy; parkinson's disease, stroke, treatment of Herpes zoster as well as postherpetic pain, tumours, collagenoses, a dysfunction of the deferent urinary tracts, haemorrhoids, nausea and vomiting, triggered for example by radiation or cytostatic therapy or motion, and painful conditions of all kinds.

Because of their long-lasting activity the compounds according to the invention are particularly suitable for the treatment and/or prevention of COPD or depression accompanied by anxiety states.

The invention therefore also relates to the use of the compounds of formula I as curative agents and pharmaceutical preparations which contain these compounds. They are preferably used on humans. The compounds according to the invention may be given intravenously, subcutaneously, intramuscularly, intraperitoneally, intranasally, by inhalation, transdermally, optionally assisted by iontophoresis or enhancers known from the literature, and by oral route.

For parenteral administration the compounds of formula I or their physiologically acceptable salts may be put into solution, suspension or emulsion, possibly with substances conventionally used for this purpose such as solubilisers, emulsifiers or other adjuvants. Suitable solvents include, for example: water, physiological saline solutions or alcohols, e.g. ethanol, propanediol or glycerol, sugar solutions such as glucose or mannitol solutions or a mixture of various solvents.

In addition, the compounds may be administered by the use of implants, e.g. of polylactide, polyglycolide or polyhydroxybutyric acid or intranasal preparations.

Compounds of formula I, wherein $R^4$ denotes $C_1$–$C_4$-alkyl, particularly methyl, are preferred.

Also preferred are compounds of formula I wherein Ar is unsubstituted phenyl or 2,3-methylenedioxyphenyl, particularly unsubstituted phenyl.

Preferred compounds of formula I are those wherein $R^3$ denotes 2-phenylethyl, wherein the phenyl group may be substituted by 1 to 3 substituents, wherein the substituents are selected independently of one another from among halogen, hydroxy, methyl, methoxy, trifluoromethyl, trifluoromethoxy, particularly wherein $R^3$ is 2-(3,5-bis-trifluoromethylphenyl)-ethyl.

Particularly preferred compounds of formula I are those wherein the group —$NR^3R^4$ is

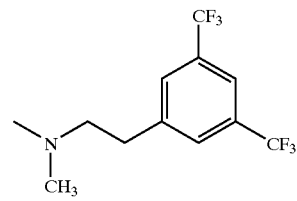

In a preferred aspect the invention relates to compounds of formula I, wherein $R^1$ denotes a cyclopropylmethyl group, and $R^2$ denotes a hydrogen atom, a $C_1$–$C_3$-alkyl group or a 3-hydroxypropyl group.

In another preferred aspect the invention relates to compounds of formula I, wherein $R^1$ denotes a 3-hydroxypropyl or 1,3-dihydroxyprop-2-yl group, and $R^2$ denotes a hydrogen atom, a $C_1$–$C_3$-alkyl group or a 2-hydroxyethyl group.

Particularly preferred are NK1 receptor antagonists which contain an amino group selected from among formulae A-1 to A-5

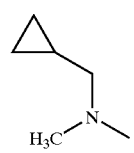

A-1

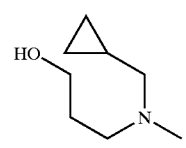

A-2

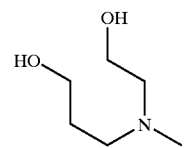

A-3

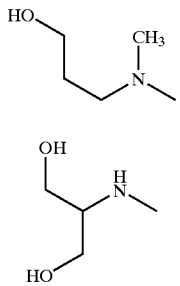

The following compounds are particularly preferred:

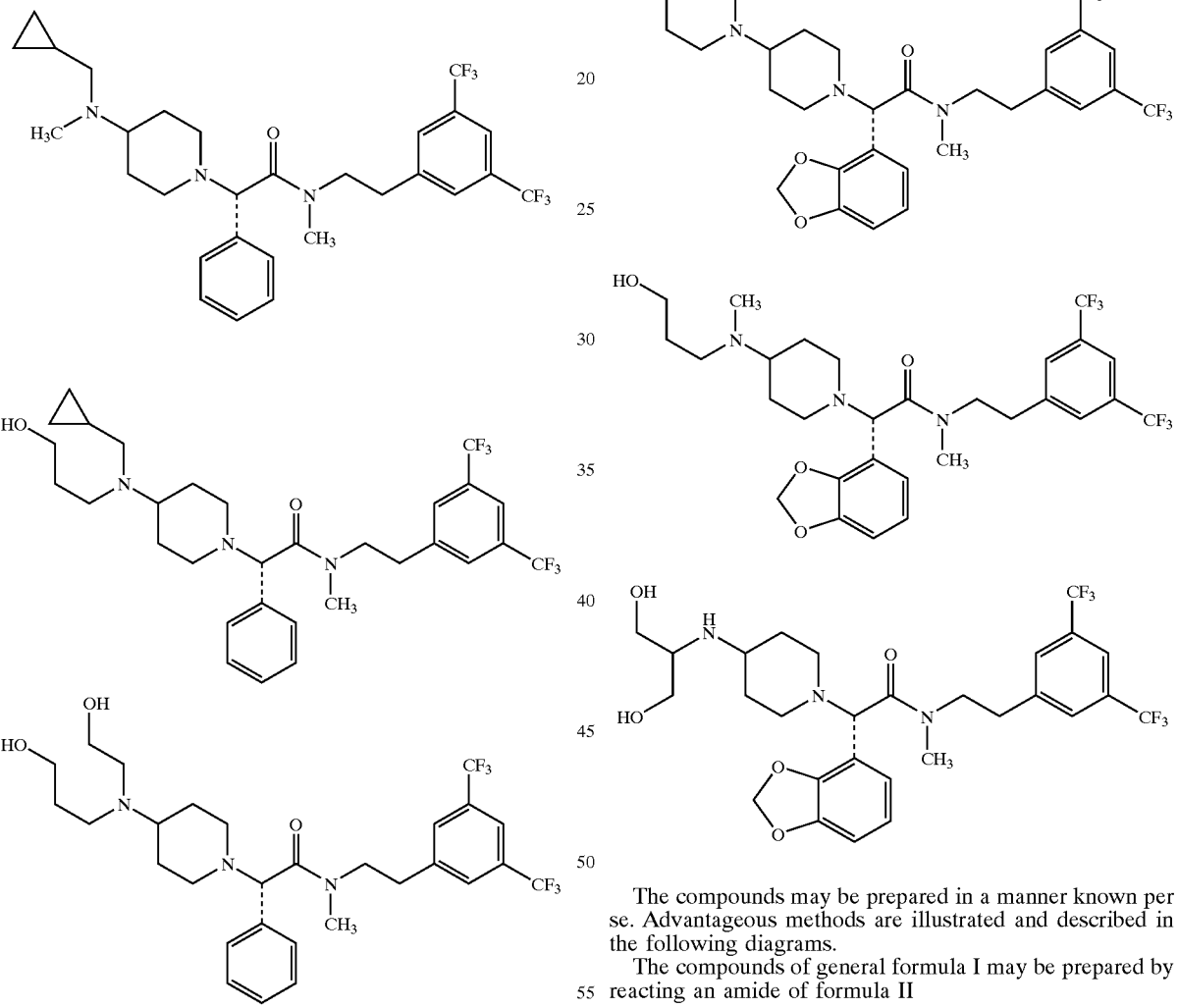

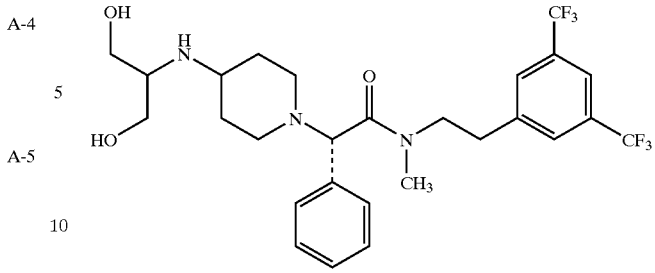

The compounds may be prepared in a manner known per se. Advantageous methods are illustrated and described in the following diagrams.

The compounds of general formula I may be prepared by reacting an amide of formula II

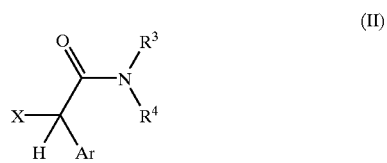

wherein X denotes a suitable leaving group, preferably halogen, alkylsulphonyloxy, particularly methylsulphonyloxy, or arylsulphonyloxy, particularly p-tolylsulphonyloxy, with a piperidine of general formula III

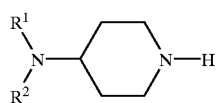

in an inert solvent in the presence of a base.

This process is illustrated by means of the following Diagram 1 for compounds wherein Ar is phenyl, $R^3$ is bis-(trifluoromethyl)-phenylethyl and $R^4$ is methyl. However, the process can be used analogously for all compounds of formula I.

First of all, 4-oxo-piperidine protected in the 1 position is reacted with an amine of formula $R^1R^2NH$, wherein $R^1$ and $R^2$ have the meanings given for formula I. In the next step the double bond of the imine or enamine group is reduced with a complex reducing agent, preferably an alkali metal alanate or alkali metal boranate, particularly sodium boranate or sodium triacetoxyborohydride. Alternatively the compounds (d) may be obtained starting from the compounds (c) by a second reductive amination by reacting with correspondingly substituted ketones or aldehydes under reductive conditions; in particular a methyl group can be introduced by reducing alkylation with formaldehyde and formic acid.

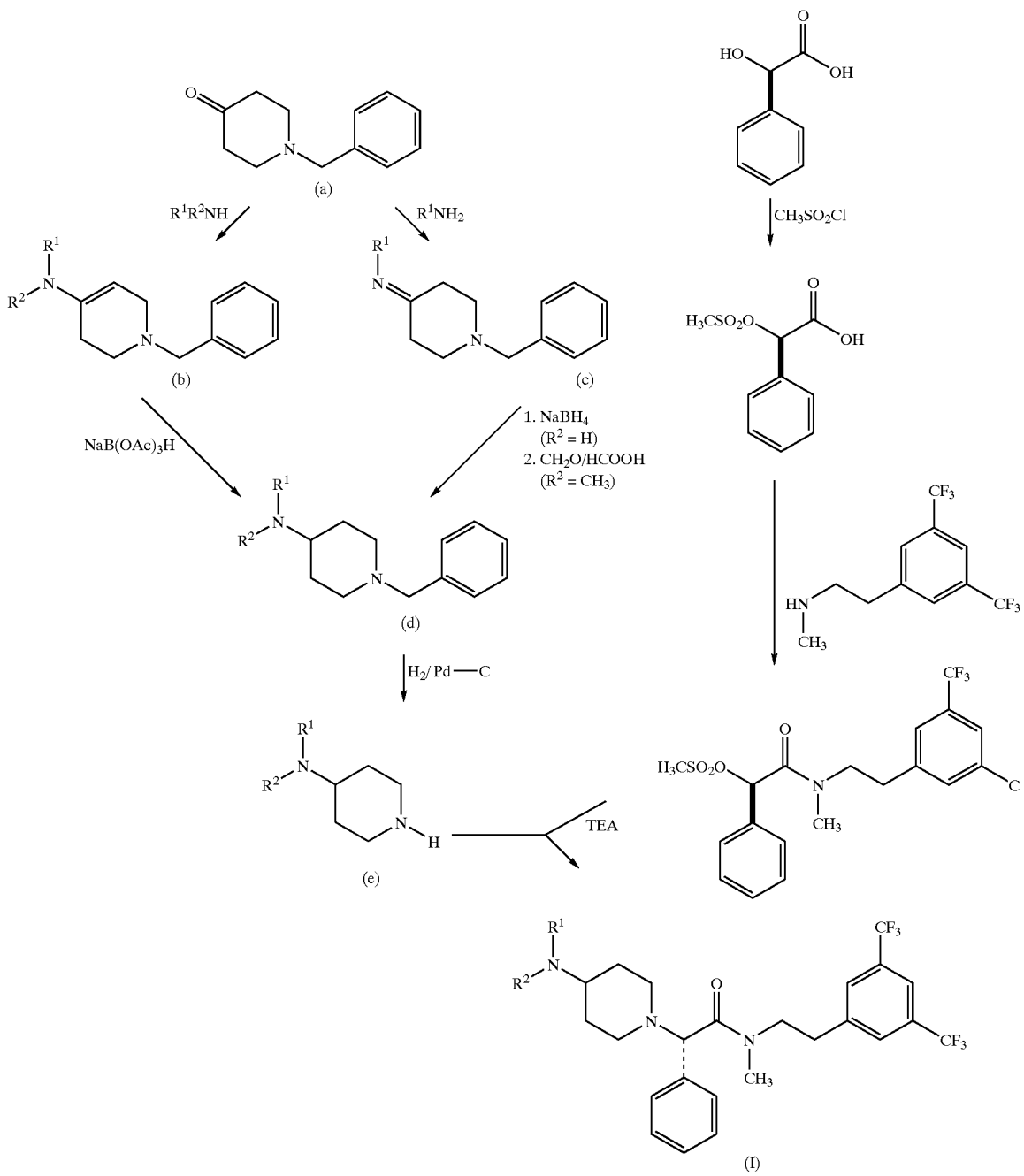

The piperidine derivative with an unsubstituted piperidine-N is then obtained by cleaving the protecting group with a cleaving reagent, preferably by hydrolysis of a Boc group or hydrogenation of a benzyl group.

The reactant for this piperazine derivative is obtained as shown in Diagram 1, on the right. (R)-Mandelic acid is reacted with methanesulphonic acid halide to obtain (R)-2-methanesulphonyloxy)-acetic acid. This is then reacted with a coupling reagent and the correspondingly substituted phenethylamine to obtain the corresponding amide, or it is converted into the corresponding acid halide (e.g. with $SOCl_2/SO_2Cl_2$) and then converted with the suitably substituted phenethylamine into the corresponding amide. In the last step the amide thus obtained is reacted with the piperidine derivative described above, while during the substitution of methanesulphonate C—N-linking takes place with simultaneous reversal of the chiral centre. The reaction is carried out in an inert solvent, preferably a polar aprotic solvent such as, for example, DMF, dimethyl acetamide, acetone, ethylmethylketone or acetonitrile in the presence of a base, preferably a tertiary amine, such as, for example, TEA or N-methylmorpholine, or an alkali metal carbonate or an alkali metal hydrogen carbonate, such as, for example, potassium carbonate at temperatures between 20° C. and 120° C. The reaction time is between 0.5 h and 48 h.

The compounds and compositions according to the invention will now be illustrated by the Examples which follow. The skilled person is aware that the Examples serve only as an illustration and are not to be regarded as limiting.

A Example of the Synthesis of Compounds According to the Invention

Example 1

N-[2-(3,5-Bis-trifluoromethyl-phenyl)-ethyl]-2-{4-[(3-hydroxy-propyl)-methyl-amino]-piperidine-1-yl}-N-methyl-2-phenyl-acetamide a) 33 g of 1-benzyl-4-piperidone and 15 g of 3-aminopropanol are combined with a catalytic amount of p-toluenesulphonic acid in 300 ml of toluene and refluxed using a water separator until the calculated amount of water has been separated off. Then the toluene is distilled off, the residue is dissolved in 250 ml of alcohol and cooled to about 5° C. A total of 6.6 g of sodium borohydride are added batchwise with stirring and stirred for 30 hours at ambient temperature. 50 ml of acetone are added, the mixture is stirred for about another half hour and the solvents are then eliminated in vacuo. The residue is combined with 100 ml of water and extracted twice with 150 ml of methylene chloride. The combined organic phases are dried. The mixture is filtered, the, the solvent is eliminated in vacuo, the residue is taken up in 80 ml of alcohol, combined with 40 ml of 32% hydrochloric acid, diluted with acetone and stirred for about one hour. The crystals precipitated are suction filtered and dried. 1-Benzyl-4-(3-hydroxypropylamino)-piperidine is obtained as the dihydrochloride.

b) The base is liberated from 47.4 g of 1-benzyl-4-(3-hydroxypropylamino)-piperidine-dihydrochloride, combined with 63 ml of 85% formic acid and 22 ml of 37% formaldehyde solution and stirred for two hours at about 90–100° C. The mixture is left to cool, 37 ml of formic acid and 11 ml of formaldehyde solution are added and stirred for another hour at about 100–110° C. The mixture is left to cool, combined with 150 ml of methanol, made alkaline with about 270 ml of 32% sodium hydroxide solution while cooling and stirred for about another 30 minutes at 40–50° C. and the methanol is then distilled off. The residue is extracted with twice 100 ml of methylene chloride, the combined methylene chloride phases are dried, filtered and the solvent is eliminated in vacuo. The residue is taken up in 80 ml of ethanol, acidified with 34 ml of 32% hydrochloric acid, combined with 100 ml of acetone and stirred. As soon as crystals are precipitated, further acetone is added. The precipitate is suction filtered, washed with acetone and dried. 42.8 g of 1-benzyl-4-[-(3-hydroxypropyl)-methylamino]-piperidine-dihydrochloride are obtained as a solid.

c) 42.8 g of 1-benzyl-4-[(3-hydroxypropyl)-methylamino]-piperidine-dihydrochloride are dissolved in 450 ml of methaol, combined with 5 g of 5% palladium/charcoal and hydrogenated at about 50° C. with hydrogen at a pressure of 4–5 bar. The catalyst is filtered off, the methanol is distilled off and the residue is stirred into acetone. Ether is added, the mixture is left to stand for about two hours and then the crystals are suction filtered. 28.7 g of 4-[(3-hydroxypropyl)-methylamino]-piperidine-dihydrochloride are obtained as a solid.

d) 9 g of 4-[-(3-hydroxypropyl)-methylamino]-piperidine-dihydrochloride are dissolved in 125 ml of DMF together with 14.5 g of N-[2-(3,5-bis-trifluoromethyl-phenyl)-ethyl]-2-methanesulphonyloxy-N-methyl-2-phenyl-acetamide (prepared analogously to the method described in WO 99/62893), combined with 20.5 g of potassium carbonate and stirred for about four hours at 80–90° C. After cooling the mixture is poured onto ice, extracted twice with 150 ml of ethyl acetate, the combined organic phases are washed twice with water and dried. The drying agent is filtered off, the solvent is eliminated in vacuo and the residue is chromatographed with methylene chloride/methanol/conc. ammonia solution 95:5:0.5 through silica gel. The fractions found to be uniform by TLC are combined and the solvent is eliminated in vacuo. The residue of 9.5 g is taken up in methanol and combined with 3.4 g of fumaric acid. Then the methanol is distilled off until only a small residue remains, acetone is added and the mixture is stirred for about 30 minutes. The crystals precipitated are suction filtered, washed with acetone and ether and dried. 9 g of N-2-N-[2-(3,5-bis-trifluoromethyl-phenyl)-ethyl]-2-{4-[(3-hydroxy-propyl)-methyl-amino]-piperidin-1-yl}-N-methyl-2-phenyl-acetamide are obtained as the colourless sesquifumarate, m.p. 139–144° C.

$^1$H-NMR (250 MHz, $CD_3OD$) δ=7.85–7.26 (8H, m); 6.71 (3H, s); 4.50; 4.49 (1H, 2s); 3.67 (2H, t, J=6.0 Hz); 3.89–3.09 (7H, m); 3.21; 3.00 (4H, m); 2.69; 2.94 (3H,); 2.77 (3H, s); 2.49–1.63 (6H, m); most signals are split by amide rotation.

(S)—N-[2-(3,5-bis-trifluoromethyl-phenyl)-ethyl]-2-{4-[(3-hydroxy-propyl)-methyl-amino]-piperidin-1-yl}-N-methyl-2-phenyl-acetamide is obtained analogously, starting from (R)-N-[2-(3,5-bis-trifluoromethyl-phenyl)-ethyl]-2-methanesulphonyloxy-N-methyl-2-phenyl-acetamide (prepared from D-(−)-mandelic acid).

Example 2

N-[2-(3,5-bis-trifluoromethyl-phenyl)-ethyl]-2-[4-(2-hydroxy-1-hydroxymethyl-ethylamino)-piperidin-1-yl]-N-methyl-2-phenylacetamide a) 2.75 g of 2-aminopropane-1,3-diol and 5.9 g of 1-benzyl-4-piperidone are dissolved in 60 ml of methylene chloride and a total of 9.9 g of sodium triacetoxyborohydride are added batchwise while cooling with ice. The mixture is left to stand overnight at ambient temperature. 60 ml of methylene chloride and some water are added, then conc. hydrochloric acid is added while cooling with ice until an acidic reaction is obtained. The mixture is stirred for about another 15 min. while cooling and then made significantly alkaline with 4 N sodium hydroxide solution. The aqueous phase is separated off, the organic phase is washed with a very little water, dried over sodium sulphate and the solvent is eliminated in vacuo. 8 g of substance are obtained which are chromatographed with methylene chloride/methanol 8:2 over 150 g of silica gel. The fractions found to be uniform by TLC are combined and the solvent is eliminated in vacuo. 7.3 g of 1-benzyl-4-(1,3-dihydroxyprop-2-ylamino)-piperdine are obtained.

b) 34.5 g of 1-benzyl-4-(1,3-dihydroxyprop-2-ylamino)-piperidine are dissolved in 400 ml of methanol, combined with 3.4 g of 20% palladium/charcoal and hydrogenated with hydrogen at 24–28° C. at 2.2 bar. Then the catalyst is filtered off and the solvent is eliminated in vacuo. 22.7 g of 4-(1,3-dihydroxyprop-2-ylamino)-piperidine are obtained as an oil which is used without further purification for the next reaction.

c) 9 g of 4-(1,3-dihydroxyprop-2-ylamino)-piperidine are reacted with 22.7 g of N-[2-(3,5-bis-trifluoromethyl-phenyl)-ethyl]-2-methanesulphonyloxy-N-methyl-2-phenyl-acetamide in 110 ml of DMF with 7.2 ml of triethylamine as base analogously to Example 1, reaction time 5 h at 60–70° C. The crude product is chromatographed over silica gel with methylene chloride/methanol 9:1. The fractions found to be uniform by TLC are combined. The oily residue is taken up in ethyl acetate and a little water, the aqueous phase is made alkaline with conc. sodium hydroxide solution. The aqueous phase is separated off, the organic phase is dried and the solvent is eliminated in vacuo. The residue is crystallised in acetone with methanesulphonic acid. 11 g of N-2-(3,5-N-[2-(3,5-bis-trifluoromethyl-phenyl)-ethyl]-2-[4-(2-hydroxy-1-hydroxymethyl-ethylamino)-piperidin-1-yl]-N-methyl-2-phenylacetamide are obtained as a colourless methanesulphonate.

$^1$H-NMR (250 MHz, CD$_3$OD) δ=7.95–7.31 (8H, m); 4.37; 4.31 ($^1$H, 2s); 3.77 (5H, m); 3.28 (1H, m); 3.05; 3.01 (4H, m); 2.74 (3H, s); 3.45–2.08 (4H, m); 2.07–1.52 (4H, m). Most signals are split by amide rotation.

(S)—N-[2-(3,5-Bis-trifluoromethyl-phenyl)-ethyl]-2-[4-(2-hydroxy-1-hydroxymethyl-ethylamino)-piperidin-1-yl]-N-methyl-2-phenylacetamide is obtaine is obtained analogously starting from (R)-N-[2-(3,5-bis-trifluoromethyl-phenyl)-ethyl]-2-methanesulphonyloxy-N-methyl-2-phenyl-acetamide (prepared from D-(–)-mandelic acid).

Example 3

N-[2-(3,5-bis-trifluoromethyl-phenyl)-ethyl]-2-[4-(cyclopropylmethyl-methyl-amino)-piperidin-1-yl]-N-methyl-2-phenyl-acetamide a) 19 g of 1-benzyl-4-piperidone are combined in 150 ml of water with 10 g of Raney nickel (moistened with methanol, rinsed with a little methanol) and 40 g of methylamine and hydrogenated for eight hours at ambient temperature under 5 bars of hydrogen. Then the catalyst is filtered off, methanol and excess methylamine are eliminated in vacuo. The mixture is extracted with ethyl acetate, the organic phase is dried over sodium sulphate, filtered and concentrated by evaporation in vacuo. 19.2 g of a yellow oil are obtained, which is used without further purification for the next reaction.

b) 18.9 g of 1-benzyl-4-methylaminopiperidine in the form of the oil prepared in a) are taken up in 250 ml of methanol, combined with 8.3 g of cyclopropane carboxaldehyde and 11.3 g of sodium cyanoborohydride. The mixture is stirred for 5 hours at 40–50° C., then for about 16 hours at ambient temperature. It is then acidified with 2 N hydrochloric acid, evaporated to dryness in vacuo and the residue is taken up in water. It is washed with ether, made alkaline with concentrated sodium hydroxide solution and extracted with ether/ethyl acetate. The organic extract is dried over sodium sulphate and freed from solvents in vacuo. 22.7 g of 1-benzyl-4-(cyclopropylmethyl-methyl-amino)-piperidine are obtained as a yellowish oil.

c) 21.5 g of the oil prepared in b) are taken up in 230 ml of methanol, combined with 2.5 g of 10% palladium/charcoal and hydrogenated at 60° C. under 5 bars of hydrogen. After 3.5 hours the catalyst is renewed and hydrogenation is continued for another five hours at 80° C. under 5 bars of hydrogen. Then the catalyst is filtered off and the solvent is eliminated in vacuo. 4-(cyclopropylmethyl-methyl-amino)-piperidine is precipitated from the residue as the dihydrochloride using ethanolic hydrochloric acid. It is then washed with ether, dried in vacuo and 12.5 g of colourless crystals are obtained.

d) 11.9 g of 4-(cyclopropylmethyl-methyl-amino)-piperidine-dihydrochloride are taken up in 400 ml of acetone and combined with 21.7 g of N-[2-(3.5-bis-trifluoromethyl-phenyl)-ethyl]-2-methanesulphonyloxy-N-methyl-2-phenyl-acetamide and 21 ml of triethylamine. The mixture is refluxed for 16 hours, then the solvent is eliminated in vacuo and the residue is taken up in 10% sodium hydrogen carbonate solution. It is extracted with ether, the combined organic phases are dried over sodium sulphate and the solvent is eliminated in vacuo. The residue is filtered with ethyl acetate/methanol/conc. ammonia solution 70:30:1 through silica gel, freed from the solvents in vacuo and crystallised in methanol with fumaric acid. The precipitate is suction filtered, washed with methanol and dried in vacuo. 9.3 g of N-[2-(3,5-bis-trifluoromethyl-phenyl)-ethyl]-2-[4-(cyclopropylmethyl-methyl-amino)-piperidin-1-yl]-N-methyl-2-phenyl-acetamide are obtained as the sesquifumarate.

$^1$H-NMR (250 MHz, CDCl$_3$) δ=7.71–7.14 (8H, m); 4.14 (1H, s); 3.81–2.46 (11H, m); 2.90; 2.82 (3H, 2s); 2.36 (3H, s); 2.23–1.48 (4H, m); 0.82 (1H, m); 0.48; 0.07 (4H, 2m). Most signals are split by amide rotation.

(S)—N-[2-(3,5-Bis-trifluoromethyl-phenyl)-ethyl]-2-[4-(cyclopropylmethyl-methyl-amino)-piperidin-1-yl]-N-methyl-2-phenyl-acetamide is obtained analogously starting from (R)—N-[2-(3,5-bis-trifluoromethyl-phenyl)-ethyl]-2-methanesulphonyloxy-N-methyl-2-phenyl-acetamide (prepared from D-(–)-mandelic acid).

Example 4

N-[2-(3,5-bis-trifluoromethyl-phenyl)-ethyl]-2-{4-[(2-hydroxy-ethyl)-(3-hydroxy-propyl)-amino]-piperidin-1-yl}-N-methyl-2-phenyl-acetamide a) 6 g of 2-hydroxyethyl-3-hydroxypropylamine and 18,9 g of 1-benzyl-4-piperidone are taken up in 250 ml of methylene chloride and combined at 0° C. with 21.2 g of sodium triacetoxyborohydride. The mixture is stirred over night at ambient temperature, then acidified with 2 N hydrochloric acid and made alkaline with concentrated sodium hydroxide solution. It is extracted with methylene chloride, the extract is dried over sodium sulphate and the solvent is eliminated in vacuo. The residue is chromatographed with ethyl acetate/methanol/conc. ammonia solution 20:80:1 over silica gel. The fractions found to be uniform by TLC are combined and the solvent is eliminated in vacuo. 2.3 g of 1-benzyl-4-[(2-hydroxy-ethyl)-(3-hydroxy-propyl)-amino]-piperidine are obtained as an oil.

b) 13.3 g of 1-benzyl-4-[(2-hydroxy-ethyl)-(3-hydroxy-propyl)-amino]-piperidine are combined with 1.5 g of 10% palladium/charcoal in 150 ml of methanol and hydrogenated at ambient temperature for 18 hours under 5 bars of hydrogen. The catalyst is renewed after 8 and 15 hours. Then the catalyst is filtered off and the filtrate, the solvent, is eliminated in vacuo. 4-[(2-hydroxy-ethyl)-(3-hydroxy-propyl)-amino]-piperidine is obtained as an oil, which is used without further purification for the next reaction.

c) 6.4 g of the oil of 4-[(2-hydroxy-ethyl)-(3-hydroxy-propyl)-amino]-piperidine prepared in b) are taken up in 300 ml of acetone, combined with 13.8 g of N-[2-(3.5-bis-trifluoromethyl-phenyl)-ethyl]-2-methanesulphonyloxy-N-methyl-2-phenyl-acetamide and 33 ml of triethylamine and refluxed for 6 hours. The mixture is cooled, the solvent is eliminated in vacuo, the residue is stirred in 10% sodium hydrogen carbonate solution and extracted with ethyl acetate. The combined organic phases are dried over sodium sulphate, the solvent is eliminated in vacuo and the residue is chromatographed with ethyl acetate/methanol/conc. ammonia solution 20:80:1 over silica gel. The fractions found to be uniform by TLC are combined and freed from the solvents in vacuo. 8.4 g of N-[2-(3,5-bis-trifluoromethyl-phenyl)-ethyl]-2-{4-[(2-hydroxy-ethyl)-(3-hydroxy-propyl)-amino]-piperidin-1-yl}-N-methyl-2-phenyl-acetamide are obtained as a yellowish-brown oil; $[\alpha]_D^{20}=+29.6°$.

$^1$H-NMR (250 MHz, CDCl$_3$) δ=7.78–7.24 (8H, m); 4.24 (1H, s); 3.78 (2H, m); 3.61 (2H, m); 3.64 (1H, m); 2.98; 2.87 (3H, 2s); 2.93 (4H, m); 2.74; 2.65 (4H, 2m); 2.88–1.77 (4H, m); 1.67 (2H, m); 1.76–1.45 (4H, m). Most signals are split by amide rotation.

Example 5

(S)—N-[2-(3.5-bis-trifluoromethyl-phenyl)-ethyl]-2-{4-[cyclopropylmethyl-(3-hydroxy-propyl)-amino]-piperidin-1-yl}-N-methyl-2-phenyl-acetamide a) 16.5 g of 3-aminopropanol and 41.7 g of 1-benzyl-4-piperidone are dissolved in 350 ml of methylene chloride and 56 g of sodium triacetoxy-borohydride are slowly added at about 10° C. The mixture is stirred overnight at ambient temperature, then acidified with dilute hydrochloric acid while cooling and then made alkaline with conc. sodium hydroxide solution. The organic phase is separated off, the aqueous phase is washed once more with 150 ml of methylene chloride. The combined organic phases are dried over sodium sulphate and the solvent is eliminated in vacuo. 32 g of 1-benzyl-4-(3-hydroxy-propylamino)-piperidine are obtained as a yellow oil, which is used without further purification in the next reaction step.

b) 13.4 g of 1-benzyl-4-(3-hydroxy-propylamino)-piperidine from the previous reaction are dissolved together with 3.8 g of cyclopropane carboxaldehyde in 250 ml of methanol and at 0° C. combined with 5.1 g of sodium cyanoborohydride. The mixture is stirred overnight at ambient temperature, then acidified with dilute hydrochloric acid while cooling and concentrated by evaporation in vacuo. The mixture is then made alkaline with conc. sodium hydroxide solution and extracted three times with 40 ml of methylene chloride. The combined organic phases are dried over sodium sulphate, filtered and the solvent is eliminated in vacuo. The residue is filtered with ethyl acetate/methanol/conc. ammonia solution 20:80:1 over silica gel. After the removal of the solvent, 10.2 g of 1-benzyl-4-[cyclopropylmethyl-(3-hydroxy-propyl)-amino]-piperidine are obtained as a yellow oil.

c) 10.2 g of 1-benzyl-4-[cyclopropylmethyl-(3-hydroxy-propyl)-amino]-piperidine are combined with 2 g of 20% palladium/charcoal in 100 ml of methanol and hydrogenated at 60° C. for 4 h under 5 bars of hydrogen. The catalyst is separated off, the solvent is eliminated in vacuo and 7.3 g of 4-[cyclopropylmethyl-(3-hydroxy-propyl)-amino]-piperidine are obtained as a yellow oil.

d) 4.7 g of 4-[cyclopropylmethyl-(3-hydroxy-propyl)-amino]-piperidine are stirred together with 9.6 g of (R)—N-[2-(3,5-bis-trifluoromethyl-phenyl)-ethyl]-2-methanesulphonyloxy-N-methyl-2-phenyl-acetamide (prepared from D-(–)-mandelic acid) and 3.4 ml of triethylamine in 200 ml of acetone for four hours at 65° C. The mixture is concentrated by evaporation in vacuo, combined with 100 ml of saturated sodium hydrogen carbonate solution and extracted with ethyl acetate. The combined organic fractions are dried over sodium sulphate and the solvent is eliminated in vacuo. The residue is chromatographed with methylene chloride/methanol 1:1 over silica gel. The fractions found to be uniform by TLC are collected and the solvents are eliminated in vacuo. 5.5 g of (S)—N-[2-(3,5-bis-trifluoromethyl-phenyl)-ethyl]-2-{4-[cyclopropylmethyl-(3-hydroxy-propyl)-amino]-piperidin-1-yl}-N-methyl-2-phenyl-acetamide are obtained as a brownish-yellow oil, $[\alpha]_D^{20}=+35.1°$ $^1$H-NMR (250 MHz, CDCl$_3$) δ=7.78–7.26 (8H, m), 4.24 (1H, s), 3.78 (2H, m); 3.63 (2H, m); 3.50 (1H, m); 2.96; 2.88 (3H, 2s); 2.93 (4H, m); 2.88–1.77 (5H, m); 2.37 (2H, d, J=6.0 Hz); 1.79–1.45 (6H, m); 0.87 (1H, m); 0.52; 0.12 (4H, 2 m). Most signals are split by amide rotation.

The compounds of Examples 6 to 8 are prepared in a similar manner or analogously to the processes described in WO 99/62893:

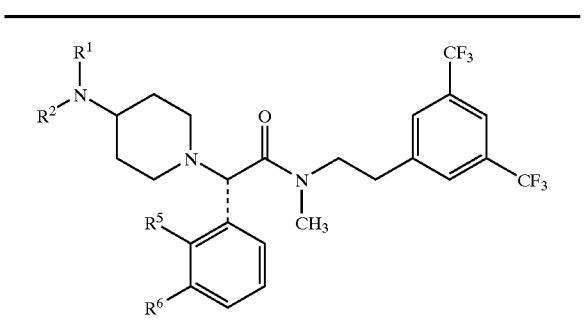

| Example | R¹ | R² | R⁵ | R⁶ |
|---|---|---|---|---|
| 6 | 3-hydroxypropyl | methyl | —O—CH₂—O— | |
| 7 | 3-hydroxypropyl | 2-hydroxyethyl | —O—CH₂—O— | |
| 8 | 1.3-dihydroxyprop-2-yl | H | —O—CH₂—O— | |

B Results of Investigations into the Compound According to the Invention

Determining the Duration of Activity

Inhibition of $NK_1$-induced Fall in Blood Pressure in Anaesthetised Guinea Pigs Guinea pigs (300–500 g) were anaesthetised with pentobarbital (50 mg/kg i.p.) and prepared for duodenal administration of the test substances and for measurement of the arterial blood pressure. A temporary drop in blood pressure was induced by the intravenous administration of an $NK_1$-agonist (0.2 μmol/kg at 30 minute intervals). After the basal value of the blood pressure had been determined the test substances were administered by intraduodenal route. Then the $NK_1$-agonist was administered intravenously every 30 min for 6 to 8 hours. The results were expressed as a percentage inhibition in the $NK_1$-induced fall in blood pressure and the $ED_{50}$ values were calculated by regression analysis.

The compounds according to the invention were compared with the compounds of the following formulae known from International Patent Application WO97/32865:

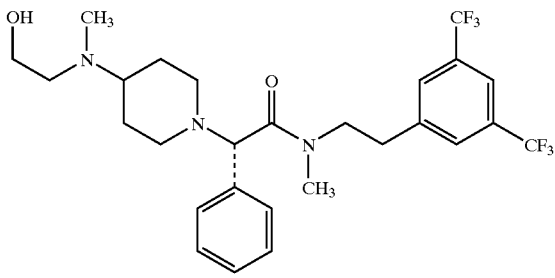

B-1

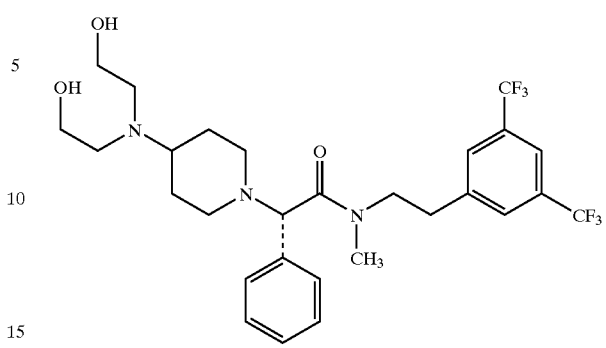

B-4

These compounds correspond to the compounds of Examples 1 and 4 in which the 3-hydroxypropyl group has been replaced by a 2-hydroxyethyl group.

The results thus obtained are listed in Table I:

| Example No. | Duration of activity [min] |
|---|---|
| 1 | >360 |
| B-1 | 120 |
| 2 | >360 |
| 3 | >360 |
| 4 | >360 |
| B-4 | 120 |
| 5 | >360 |
| 6 | >360 |
| 7 | >360 |
| 8 | >360 |

C Formulations of Compounds According to the Invention

| Injectable solution |
|---|
| 200 mg active substance* |
| 1.2 mg monopotassium dihydrogen phosphate = $KH_2PO_4$ ) |
| 0.2 mg disodium hydrogen phosphate =                       ) (buffer) |
|     $NaH_2PO_4 \cdot 2H_2O$                                ) |
| 94 mg sodium chloride            )  (isotonic agent) |
| or                               ) |
| 520 mg glucose                   ) |
| 4 mg albumin                     (protease protection) |
| q.s.   sodium hydroxide solution ) |
| q.s.   hydrochloric acid         )  ad pH 6 |
| ad 10 ml water for injections |

| Injectable solution |
|---|
| 200 mg active substance* |
| 94 mg sodium chloride |
| or |
| 520 mg glucose |
| 4 mg albumin |
| q.s.   sodium hydroxide solution ) |
| q.s.   hydrochloric acid         )  ad pH 9 |
| ad 10 ml water for injections |

| Lyophilisate |
|---|
| 200 mg active substance* |
| 520 mg mannitol (isotonic agent/bulking agent) |
| 4 mg albumin |
| solvent 1 for lyophilisate |
| 10 ml water for injections |
| solvent 2 for lyophilisate |

| | |
|---|---|
| 20 mg | Polysorbat ® 80 = Tween ® 80 (surfactant) |
| 10 ml | water for injections |

*active substance: compound according to the invention, e.g. one of Examples 1 to 8 dose for humans weighing 67 kg: 1 to 500 mg

We claim:

1. A compound of formula (I):

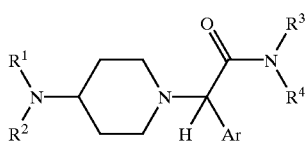

or a pharmaceutically acceptable salt thereof, wherein
- $R^1$ denotes 1,3-dihydroxyprop-2-yl,
- $R^2$ denotes hydrogen, $C_1$–$C_6$alkyl, ω-hydroxy-$C_2$–$C_4$-alkyl, 1,3-dihydroxyprop-2-yl or $C_3$–$C_6$-cycloalkylmethyl,
- Ar denotes unsubstituted phenyl or phenyl which is 1- to 5-substituted by halogen, hydroxy, $C_1$–$C_4$-alkyl, $C_1$–$C_4$-alkoxy, $C_1$–$C_4$-fluoroalkyl, $C_1$–$C_4$-fluoroalkoxy or —OCH$_2$O—;
- $R^3$ denotes phenyl-$C_1$–$C_4$-alkyl, wherein the phenyl group may be substituted by 1 to 3 substituents, wherein the substituents independently of one another are selected from halogen, hydroxy, $C_1$–$C_4$-alkyl, $C_1$–$C_4$-alkoxy, $C_1$–$C_4$-fluoroalkyl, and $C_1$–$C_4$-fluoroalkoxy; and
- $R^4$ denotes hydrogen, $C_1$–$C_4$-alkyl, $C_3$–$C_8$-cycloalkyl, CH$_2$COOH, —CH$_2$C(O)NH$_2$, —OH or phenyl-$C_1$–$C_4$-alkyl.

2. A compound according to claim 1, wherein $R^4$ is $C_1$–$C_4$-alkyl.

3. A compound according to claim 1, wherein Ar is unsubstituted phenyl or 2,3-methylenedioxyphenyl.

4. A compound according to claim 2, wherein Ar is unsubstituted phenyl or 2,3-methylenedioxyphenyl.

5. A compound according to claim 1, wherein $R^3$ denotes 2-phenylethyl, where the phenyl group may be substituted by 1 to 3 substituents, wherein the substituents independently of one another are each selected from among halogen, hydroxy, methyl, methoxy, trifluoromethyl or trifluoromethoxy.

6. A compound according to claim 2, wherein $R^3$ denotes 2-phenylethyl, where the phenyl group may be substituted by 1 to 3 substituents, wherein the substituents independently of one another are each selected from among halogen, hydroxy, methyl, methoxy, trifluoromethyl or trifluoromethoxy.

7. A compound according to claim 3, wherein $R^3$ denotes 2-phenylethyl, where the phenyl group may be substituted by 1 to 3 substituents, wherein the substituents independently of one another are each selected from among halogen, hydroxy, methyl, methoxy, trifluoromethyl or trifluoromethoxy.

8. A compound according to claim 4, wherein $R^3$ denotes 2-phenylethyl, where the phenyl group may be substituted by 1 to 3 substituents, wherein the substituents independently of one another are each selected from among halogen, hydroxy, methyl, methoxy, trifluoromethyl or trifluoromethoxy.

9. A compound according to claim 1, wherein $R^3$ is 2-(3,5-bistrifluoromethylphenyl)-ethyl.

10. A compound according to claim 2, wherein $R^3$ is 2-(3,5-bistrifluoromethylphenyl)-ethyl.

11. A compound according to claim 3, wherein $R^3$ is 2-(3,5-bistrifluoromethylphenyl)-ethyl.

12. A compound according to claim 4, wherein $R^3$ is 2-(3,5-bistrifluoromethylphenyl)-ethyl.

13. A compound according to claim 1, wherein the group —NR$^3$R$^4$ is

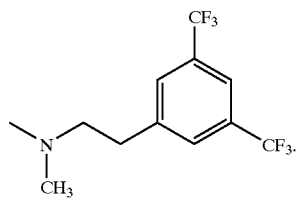

14. A compound according to claim 2, wherein the group —NR$^3$R$^4$ is

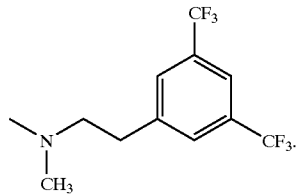

15. A compound according to claim 3, wherein the group —NR$^3$R$^4$ is

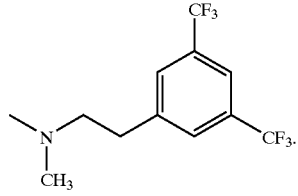

16. A compound according to claim 4, wherein the group —NR$^3$R$^4$ is

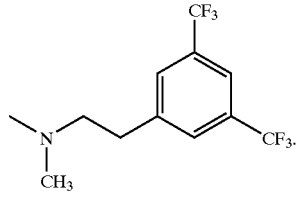

17. A compound according to claim 1, wherein
$R^1$ denotes a 1,3-dihydroxyprop-2-yl group, and
$R^2$ denotes a hydrogen atom, a $C_1$–$C_3$-alkyl group or a 2-hydroxyethyl group.

18. A compound according to claim 2, wherein
$R^1$ denotes a 1,3-dihydroxyprop-2-yl group, and
$R^2$ denotes a hydrogen atom, a $C_1$–$C_3$-alkyl group or a 2-hydroxyethyl group.

19. A compound according to claim 3, wherein
$R^1$ denotes a 1,3-dihydroxyprop-2-yl group, and
$R^2$ denotes a hydrogen atom, a $C_1$–$C_3$-alkyl group or a 2-hydroxyethyl group.

20. A compound according to claim 4, wherein
R¹ denotes a 1,3-dihydroxyprop-2-yl group, and
R² denotes a hydrogen atom, a $C_1$–$C_3$-alkyl group or a 2-hydroxyethyl group.

21. A compound having the following formula:

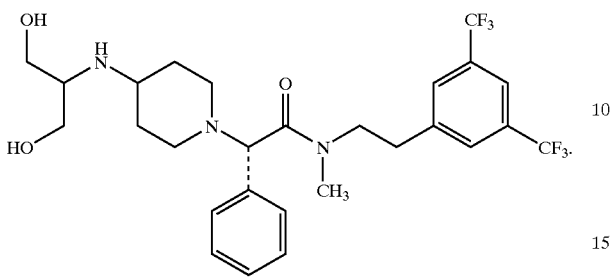

22. A process for preparing a compound of formula I according to claim 1, said process comprising reacting an amide of formula II

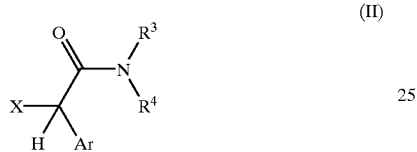

(II)

wherein Ar, R³ and R⁴ are as defined in claim 1 and X denotes a suitable leaving group,
with a piperidine of formula III

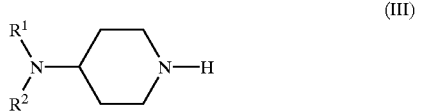

(III)

wherein R¹ and R² are as defined in claim 1, in an inert solvent in the presence of a base.

23. A pharmaceutical composition comprising a compound according to claim 1 and one or more pharmaceutically acceptable carriers and excipients.

24. A method of treating an illness selected from inflammatory and allergic conditions of the airways, eyes, skin, the gastro-intestinal tract, joints, bones and bladder; and central nervous system diseases comprising administering to a host in need of such treatment a therapeutically effective amount of a compound according to claim 1.

25. A method of treating an illness selected from:

asthma, chronic bronchitis, hyperreactive airways, emphysema, rhinitis, COPD, pulmonary hypertension, cystic fibrosis, coughs;

conjunctivitis, iritis;

dermatitis in contact eczema, neurodermatitis, pruritus, urticaria, psoriasis, sunburn, burns, insect bites, rosacea, itching, sensitive or hypersensitive skin;

gastric and duodenal ulcers, ulcerative colitis, Crohn's disease, inflammatory bowel disease, irritable colon, Hirschsprung's disease, motility problems;

rheumatoid arthritis, reactive arthritis, arthrosis, osteoporosis and Reiter's syndrome;

irritable bladder, incontinence, urinary urgency, urethritis, colic and cystitis; restless leg syndrome;

dementia, Alzheimer's disease, schizophrenia, psychoses, anxiety states, alcohol or drug dependency, sexual dysfunctions, eating disorders, depression, headaches, epilepsy, Parkinson's disease, stroke;

Herpes zoster, postherpetic pain, tumors, collagenoses, a dysfunction of the deferent urinary tracts, haemorrhoids, nausea and vomiting, and pain, comprising administering to a host in need of such treatment a therapeutically effective amount of a compound according to claim 1.

26. A method according to claim 24, wherein the illness is selected from:
COPD, anxiety states and depression.

27. A compound having the following formula:

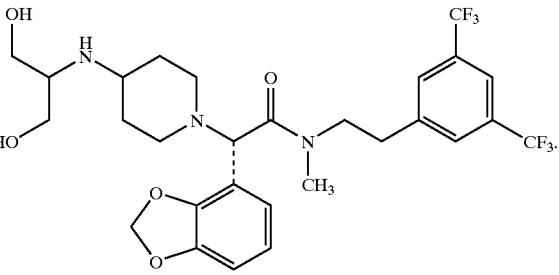

* * * * *